United States Patent [19]

Morinaka et al.

[11] 4,298,610
[45] Nov. 3, 1981

[54] ESTER DERIVATIVES OF QUINOLOPYRAN-4-ONE-2-CARBOXYLIC ACIDS AND ANTIALLERGIC ANTASTHMATICS

[75] Inventors: Yasuhiro Morinaka, Ami; Kazuo Takahashi, Ibaragi, both of Japan

[73] Assignee: Mitsubishi Yuka Pharmaceutical Co., Ltd., Tokyo, Japan

[21] Appl. No.: 43,906

[22] Filed: May 30, 1979

[30] Foreign Application Priority Data

Jun. 5, 1978 [JP] Japan ................................ 53/67448

[51] Int. Cl.$^3$ .................... C07D 491/04; A61K 31/47
[52] U.S. Cl. ...................................... 424/256; 546/92
[58] Field of Search .......................... 546/92; 424/256

[56] References Cited

U.S. PATENT DOCUMENTS 4,086,349  4/1978  Morinaka .............................. 546/92

Primary Examiner—Alan L. Rotman
Attorney, Agent, or Firm—Oblon, Fisher, Spivak, McClelland & Maier

[57] ABSTRACT

Novel ester derivatives of quinolopyran-4-one-2-carboxylic acids and the tautomers thereof are provided, the ester groups being specified and restricted. These novel compounds are especially useful as antiallergic antasthmatics or remedies for asthma, and can be administered orally with long duration of action.

9 Claims, No Drawings

ESTER DERIVATIVES OF QUINOLOPYRAN-4-ONE-2-CARBOXYLIC ACIDS AND ANTIALLERGIC ANTASTHMATICS

BACKGROUND OF THE INVENTION

1. Field of the Invention

This invention relates to novel derivatives of quinolopyran-4-one-2-carboxylic acid esters and to their uses as medical drugs.

These novel compounds are useful as antiallergic remedies for asthma or antasthmatics, and can be orally administered. Moreover, they have long duration of action.

2. Prior Art

Cox et al have reported that disodium cromoglycate developed recently is effective for allergic asthma [Adv. in Drug Res. 5, 115 (1970)]. This compound is considered to exhibit its effectiveness by inhibiting the release of chemical mediators from mast cells which have resulted from the antigen-antibody reaction caused by the reagin antibody. This compound, however, is disadvantageous in that it cannot be absorbed via oral administration and has a short duration of action.

On the other hand, the present inventors have provided the derivatives of quinolopyran-4-one-2-carboxylic acids which are similar to the compounds of the present invention represented by the general formula [I], which will be described in detail hereinafter, and found that the derivatives are useful as antiallergic remedies for asthma. See, Japanese Unexamined Patent Publication Nos. 17,498/77 and 109,000/77, which are equivalent to, e.g., U.S. Pat. No. 4,086,349.

In the present invention, it is essential that the present compounds be esters of the quinolopyran-4-one-2-carboxylic acids with the specified alcohols (R—OH), wherein the definition of R is given below with respect to the general formula [I]. The ester derivatives of the acids wherein R of the alcohol is a $C_1$ to $C_5$ alkyl, phenyl and benzyl are disclosed in the above-mentioned Unexamined Patent Publication No. 17,498/77. In the specification, methyl, ethyl and n-butyl alcohols are given as specific examples of $C_1$ to $C_5$ alkyls. However, neither physical property data nor pharmacological data are given with respect to these five species of esters. (The invention disclosed in the Unexamined Patent Publication No. 17,498/77 is described as a process for preparation, and thus both the physical property data and the pharmacological data are not shown therein.) Moreover, while it is disclosed in the Unexamined Publication that the compounds may be in the form of esters as well as acids and salts, the specification is also silent as to specific dosages for oral administration when the compounds are in the form of esters, although the general dosages for oral administration of these compounds are given.

In the Unexamined Patent Publication No. 109,000/77, the antiallergic remedies for asthma comprising the quinolopyran-4-one-2-carboxylic acid derivatives or the salts thereof and the dosages for oral administration thereof are described.

The derivatives of quinolopyran-4-one-2-carboxylic acids, which have free carboxylic groups, may be thus administered orally. These compounds themselves, however, are inactivated in the stomach and are required to be in the form of entric drugs to prevent the inactivation in the stomach and to commence absorption in the duodenum. Such methods of administration are practically difficult, and the effectiveness will fluctuate from person to person.

Thus, in the prior inventions by the present inventors, these compounds in the form of free acids may be said to have problems of oral administration thereof.

SUMMARY OF THE INVENTION

It is an object of the present invention to solve the above described problems. This object has been achieved by providing the esters, specified and restricted herein, of quinolopyran-4-one-2-carboxylic acid derivatives.

The ester derivatives of quinolopyran-4-one-2-carboxylic acids in accordance with the present invention are the compounds represented by the following general formula [I] or the tautomers thereof,

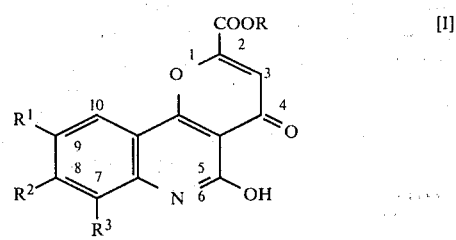

wherein, $R^1$, $R^2$ and $R^3$ each stands for hydrogen, an alkyl group having 1 to 5 carbon atoms, an alkoxyl group having 1 to 5 carbon atoms, benzyloxy group, a halogen atom, an alkoxycarbonyl group having 2 to 6 total carbon atoms, an aryl group having 6 to 10 carbon atoms, or an alkylenedioxy group having 1 to 3 carbon atoms formed by two alkoxyl groups which are selected from $R^1$, $R^2$ and $R^3$ and bonded together, respectively; and R is an alcohol residue having 5 or 6 carbon atoms selected from the group consisting of 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl, and 3-methyl-2-pentyl.

The antiallergic remedies for asthma in accordance with the present invention comprise the ester derivatives of quinolopyran-4-one-2-carboxylic acids represented by the above general formula [I] or the tautomers thereof.

One of the important features of the present invention is that the compounds represented by the formula [I], wherein the substituent R is a specified group to form an ester group, exhibit a high efficacy via oral administration, whereas the conventional compounds represented by the formula [I] wherein R is H do not show such efficacy per os. This fact is very advantageous in that the compounds of the present invention are used as medical drugs by a simple mode of administration.

Another advantageous feature of the present invention is that the compounds according thereto afford a longer duration of action by oral administration. A medicine of this type is useful as a preventive medicine for asthma and is generally required to be administered for a long period of time before the symptoms of asthma appear. The cromoglycate now on the market has a short duration of action and requires 3 to 4 administrations a day. A medical drug having a longer duration of action is advantageous in that the number of times of administration can be decreased.

DETAILED DESCRIPTION OF THE INVENTION

1. Selection of the Substituent R

Various 5-hydroxy-quinolopyran-4-one-2-carboxylic acid esters in terms of the R group represented by the general formula [I] were prepared. The suitable R groups of the compounds were selected according to the effects obtained by oral administration. In order to estimate the efficacy of each compound as an anti-allergic antasthmatic, the efficacy was evaluated according to a passive cutaneous anaphylaxis test (P.C.A.) on rats.

ANAPHYLAXIS TESTS

To SLC Wister rats were administered intracutaneously egg white albumin recrystallized 5 times and Bodetallapertussis Vaccine, and serum was collected after 13 days from the rats. The serum contained an antibody having similar properties to human reagin and showed an antibody titre of not less than 256. The serum was diluted 128 times and it was then administered intracutaneously to the back of the rats. After 48 hours, the compounds of the present invention in the quantities shown in Table 1 which had been suspended in 1% tragacanth solution were administered orally to the rats. A physiological salt solution in which egg white albumin and a dye (Evans' blue) were dissolved was administered intravenously, 30 minutes after the oral administration, to the rats; and 30 minutes thereafter the back skins of the rats were peeled off. The dye that transuded from the peeled skin was extracted with $Na_2SO_4$ and acetone, and the quantities of the dye were measured by colorimetry at 620 m $\mu$.

The results of evaluation are shown in Table 1.

TABLE 1

| Parent carboxylic acid | Substituent R | Nr. of carbon atoms of R | Dose (mg/kg) | Percent inhibition (%) |
|---|---|---|---|---|
| 7,8-dimethyl-5-hydroxyquinolo[4,3-b]pyran-4-one-2-carboxylic acid | methyl | 1 | 100 | 39.4 |
| | ethyl | 2 | 100 | 36.1 |
| | isopropyl | 3 | 30 | 7.3 |
| | n-butyl | 4 | 30 | 48.8 |
| | 2-methyl-1-propyl | 4 | 30 | 2.5 |
| | n-pentyl | 5 | 30 | 26.5 |
| | 3-methyl-1-butyl | 5 | 30 | 95.5 |
| | 2-methyl-1-butyl | 5 | 30 | 99.8 |
| | 2,2-dimethyl-1-propyl | 5 | 30 | 93.2 |
| | 2-pentyl | 5 | 30 | 95.1 |
| | 3-pentyl | 5 | 30 | 65.3 |
| | 3-methyl-2-butyl | 5 | 30 | 22.6 |
| | n-hexyl | 6 | 30 | 72.0 |
| | 4-methyl-1-pentyl | 6 | 30 | 78.5 |
| | 2-methyl-1-pentyl | 6 | 30 | 97.9 |
| | 3-methyl-1-pentyl | 6 | 30 | 80.8 |
| | 4-methyl-2-pentyl | 6 | 30 | 67.6 |
| | 2-hexyl | 6 | 30 | 94.7 |
| | 2-ethyl-1-butyl | 6 | 30 | 49.1 |
| | 3-hexyl | 6 | 30 | 96.1 |
| | 3,3-dimethyl-1-butyl | 6 | 30 | 26.5 |
| | 3-methyl-2-pentyl | 6 | 30 | 68.3 |
| | 3,3-dimethyl-2-butyl | 6 | 30 | 42.7 |
| | 2-methyl-3-pentyl | 6 | 30 | 32.1 |
| | 1-cyclohexyl | 6 | 30 | 33.7 |
| | n-heptyl | 7 | 30 | 36.3 |
| | n-octyl | 8 | 30 | 39.3 |
| | n-decyl | 10 | 30 | 4.7 |
| | n-dodecyl | 12 | 30 | −26.2 |
| | benzyl | 7 | 100 | 13.2 |
| | 3-phenyl-1-propyl | 9 | 30 | −7.2 |
| | 2,3-dihydroxypropyl | 3 | 100 | 8.6 |
| | 2-hydroxy-ethyl | 2 | 100 | 21.4 |
| | H | 0 | 100 | 5.5 |
| 9-methyl-5-hydroxyquinolo[4,3-b]pyran-4-one-2-carboxylic acid | 3-methyl-1-butyl | 5 | 30 | 87.2 |
| | 2-methyl-1-butyl | 5 | 30 | 83.0 |
| | 2,2-dimethyl-1-propyl | 5 | 30 | 58.4 |
| | 2-pentyl | 5 | 30 | 70.0 |
| | 2-methyl-1-pentyl | 6 | 30 | 83.8 |
| | 3-hexyl | 6 | 30 | 81.8 |
| 9-chloro-5-hydroxyquinolo[4,3-b]pyran-4-one-2-carboxylic acid | 3-methyl-1-butyl | 5 | 30 | 59.5 |
| 9-ethoxycarbonyl-5-hydroxyquinolo[4,3-b]pyran-4-one-2-carboxylic acid | 3-methyl-1-butyl | 5 | 30 | 52.7 |
| 9-n-butyl-5-hydroxyquinolo[4,3-b]pyran-4-one-2-carboxylic acid | 3-methyl-1-butyl | 5 | 30 | 64.5 |
| 8,9-dimethoxy-5-hydroxyquinolo[4,3-b]pyran-4-one-2-carboxylic acid | 3-methyl-1-butyl | 5 | 30 | 67.3 |

From the results shown in Table 1, it is noted that the compounds wherein the substituent R is an alcohol residue having 5 to 6 carbon atoms and especially alcohol residues as indicated below have higher efficacies.

alcohol residue with 5 carbon atoms
3-methyl-1-butyl, 2-methyl-1-butyl, 2,2-dimethyl-1-propyl, 2-pentyl, 3-pentyl;

alcohol residue with 6 carbon atoms
n-hexyl, 4-methyl-1-pentyl, 2-methyl-1-pentyl, 3-methyl-1-pentyl, 4-methyl-2-pentyl, 2-hexyl, 3-hexyl, 3-methyl-2-pentyl.

The compounds of the present invention containing the following groups, out of the above-listed alcohol residues, especially have higher efficacies.

3-methyl-1-butyl, 2-methyl-1-butyl, 2,2-dimethyl-1-propyl, 2-pentyl, 2-methyl-1-pentyl, 2-hexyl and 3-hexyl.

2. Duration of Action

In the above-described passive cutaneous anaphylaxis test of the rats, the intervals between the oral administration of the present compounds and the administration of egg white albumin and the dye were variously changed to observe the changes in the effect of the compounds depending upon the intervals.

As a representative compound of the present invention, 2-methyl-1-pentyl ester of 7,8-dimethyl-5- hydroxy-quinolo[4,3-b]pyran-4-one-2-carboxylic acid was used. The percent inhibition is shown in Table 2 when the compound was orally administered in a ratio of 30 mg/kg.

TABLE 2

| Period of time | 10 min. | 20 min. | 30 min. | 40 min. | 1 hr. | 2 hrs. | 3 hrs. | 4 hrs. |
|---|---|---|---|---|---|---|---|---|
| Percent inhibition (%) | 96.5 | 98.5 | 95.0 | 93.0 | 92.5 | 72.5 | 61.5 | 53.0 |

3. Examples of the Compounds

Specific examples of the compounds of the present invention represented by the general formula [I] are set forth below. Here, the symbol [R] stands for 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl, or 3-methyl-2-pentyl.

9-methyl-5-hydroxy-quinolo[4,3-b]pyran-4-one-2-caboxylic acid [R] ester, 8-methyl-5-hydroxy-quinolo[4,3-b]pyran-4-one-2-carboxylic acid [R] ester, 7-methyl-5-hydroxy-quinolo[4,3-b]pyran-4-one-2-carboxylic acid [R] ester, 9-ethyl-5-hydroxy-quinolo[4,3-b]pyran-4-one-2-carboxylic acid [R] ester, 9-n-butyl-5-hydroxy-quinolo[4,3-b]pyran-4-one-2-carboxylic acid [R] ester, 9-t-butyl-5-hydroxy-quinolo[4,3-b]pyran-4-one-2-carboxylic acid [R] ester, 7,8-dimethyl-5-hydroxy-quinolo[4,3-b]pyran-4-one-2-carboxylic acid [R] ester, 7,9-dimethyl-5-hydroxy-quinolo[4,3-b]pyran-4-one-2-carboxylic acid [R] ester, 9-methoxy-5-hydroxy-quinolo[4,3-b]pyran-4-one-2-carboxylic acid [R] ester, 7-methoxy-5-hydroxy-quinolo[4,3-b]pyran-4-one-2-carboxylic acid [R] ester, 8,9-dimethoxy-5-hydroxy-quinolo[4,3-b]pyran-4-one-2-carboxylic acid [R] ester, 9-butoxy-5-hydroxy-quinolo[4,3-b]pyran-4-one-2-carboxylic acid [R] ester, 8,9-methylenedioxy-5-hydroxy-quinolo[4,3-b]-pyran-4-one-2-carboxylic acid [R] ester, 9-benzyloxy-5-hydroxy-quinolo[4,3-b]pyran-4-one-2-carboxylic acid [R] ester, 9-chloro-5-hydroxy-quinolo[4,3-b]pyran-4-one-2-carboxylic acid [R] ester, 7-chloro-5-hydroxy-quinolo[4,3-b]pyran-4-one-2-carboxylic acid [R] ester, 9-bromo-5-hydroxy-quinolo[4,3-b]pyran-4-one-2-carboxylic acid [R] ester, 9-fluoro-5-hydroxy-quinolo[4,3-b]pyran-4-one-2-carboxylic acid [R] ester, 9-ethoxycarbonyl-5-hydroxy-quinolo[4,3-b]pyran-4-one-2-carboxylic acid [R] ester, 7-methyl-8-chloro-5-hydroxy-quinolo[4,3-b]pyran-4-one-2-carboxylic acid [R] ester, and 9-phenyl-5-hydroxy-quinolo[4,3-b]pyran-4-one-2-carboxylic acid [R] ester.

It should be understood that the compounds represented by the formula [I] are indicated herein in the form of 5-hydroxy compounds for the sake of convenience, but they may be in the form of the following tautomers [I'].

In view of the nature of 2-hydroxy-quinoline and the like, it seems that the above-described formula [I'] is more important. Of course, the compounds represented by the formula [I'] fall within the scope of the present invention.

4. Process for preparation

The compounds of the present invention are in the form of esters. The compounds can thus be prepared by reacting a carboxylic acid represented by the general formula [I] wherein R is H with an alcohol represented by the general formula R—OH under an ester-forming condition. In this case "the reactions under an ester-forming conditions" include, for example, a reaction of a functional derivative of a carboxylic acid or alcohol, such as a carboxylic acid halide, with an alcohol or a carboxylic acid or its functional derivative, such as an alcohol, through dehydrohalogenation in this particular example, and a direct dehydration-condensation reaction of a carboxylic acid and an alcohol.

The compounds of the present invention can also be prepared by deriving the compound from its precursor in view of the moiety other than the substituent R.

Some specific examples of the process are set forth below. Processes (1) and (6) are preferable.

(1) Acid halide process

-continued

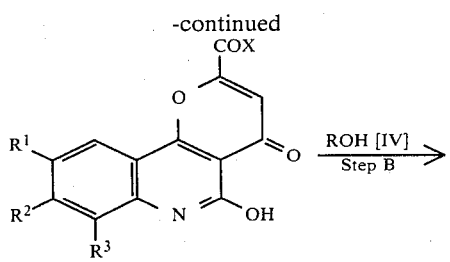

[III]

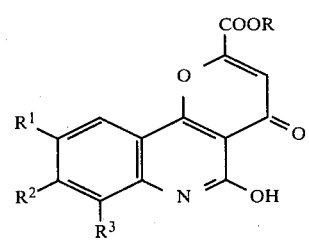

[I]

wherein, $R^1$, $R^2$ and $R^3$ have the same meanings as in the above-mentioned definitions, and X stands for Cl, Br or I.

A starting carboxylic acid represented by the general formula [II] or its salt is treated with a halogenating agent to prepare an acid halide represented by the general formula [III] (step A). The resulting acid halide is then reacted with an alcohol represented by the general formula [IV] to obtain a carboxylic acid ester represented by the general formula [I] (step B).

(1) Step A

In the step A, the starting carboxylic acid [II] or its salt is subjected to reaction with a halogenating agent in the presence or absence of an organic solvent to prepare the corresponding carboxylic acid halide [III]. The resulting halide [III] can be isolated by a conventional method but can be further treated in the following step B without such isolation if so desired.

(a) the starting material [II]

The starting carboxylic acids [II] and the salts thereof can be prepared in accordance with the processes disclosed in Japanese Unexamined Patent Publication Nos. 17,498/77 and 109,000/77.

Specific examples of the carboxylic acids [II] are 5-hydroxy-quinolo[4,3-b]pyran-4-one-2-carboxylic acid derivatives which have been unsubstituted or substituted with 7-methyl, 8-methyl, 9-methyl, 9-ethyl, 9-isopropyl, 9-n-butyl, 9-t-butyl, 7-methoxy, 8-methoxy, 9-methoxy, 9-isopropyloxy, 9-butoxy, 7,8-methylenedioxy, 9-benzyloxy, 7-chloro, 8-chloro, 9-chloro, 9-bromo, 9-iodo, 9-fluoro, 9-ethoxycarbonyl, 9-butoxycarbonyl, 9-phenyl, 7,8-dimethyl, 7,9-dimethyl, 8,9-dimethyl, 7,8-dibutyl, 7,9-dimethoxy, 8,9-dimethoxy, 7,9-dibutoxy, 7-methyl-8-chloro, 8,9-dichloro, and the like.

Examples of salts of these carboxylic acids are the salts of metals such as sodium, potassium, magnesium, calcium, and aluminium and the salts of cations such as ammonium, triethylamine, tris(hydroxymethyl)aminomethane, methylamine and pyridine.

| (b) Suitable reaction conditions | |
|---|---|
| (i) Temperature: | of the order of $-20°$ to $200°$ C., preferably $0°$ to $150°$ C. |
| (ii) Time: | of the order of 10 min. to 2 days, preferably 30 min. to 10 hours. |
| (iii) Halogenating agents: | thionyl chloride, phosphorus trichloride, phosphorus pentachloride, phosphorus oxychloride, etc. The agent is used in a molar ratio to the starting material of the order of 0.5 to about 50, preferably of from 1 to 20. |
| (iv) Solvents: | When the reaction is carried out in the presence of a solvent, a solvent such as halogenated alkanes (e.g., dichloromethane, chloroform), aromatic hydrocarbons (e.g., benzene, toluene, xylene), and dimethylformamide is used in a quantity, in terms of weight ratio to the starting material, of the order of 1 to 100, preferably of from 5 to 50. |

In order to isolate the product carboxylic acid halides [III], the halogenating agent and solvent are concentrated, and thereafter water is added thereto. The product is then subjected to extraction with an organic solvent such as dichloromethane or chloroform. When thionyl chloride is used as the halogenating agent, the product carboxylic acid halides are concentrated to dryness and then purified, and they can be used without isolation in the succeeding step B.

(2) Step B

The carboxylic acid halides [III] obtained in the step A are used as starting material, and are subjected to reaction with the alcohol represented by the general formula [IV] in the presence or absence of an organic solvent, and if desired in the presence of a base, to prepare the carboxylic acid esters represented by the general formula [I].

(a) Suitable reaction conditions (i) Temperature: of the order of $-30°$ to $200°$ C., preferably $-10°$ to $150°$ C.

(ii) Time: of the order of 30 min. to 1 day, preferably 1 to 10 hours.

(iii) Base: In the case where a base is to be used, for example, an organic amine such as triethylamine, dimethyl aniline, or pyridine, or an alkali such as sodium hydroxide, potassium hydroxide, potassium carbonate, sodium carbonate, or sodium hydride can be used in a quantity, in terms of molar ratio to the starting material, of the order of 0.5 to about 10, preferably of from 1 to 5.

(iv) Solvents: In the case where a solvent is to be used, for example, a halogenated alkane such as dichloromethane or chloroform, an aromatic hydrocarbon such as benzene, toluene or xylene, an ether such as dioxane or tetrahydrofuran, a ketone such as acetone or methyl ethyl ketone, dimethylformamide, dimethylsulfoxide, or the like, can be used in a quantity, in terms of weight ratio to the starting material, of the order of 1 to 100, preferably of from 1 to 50.

(v) Alcohols: An alcohol represented by the general formula [IV] is used in a quantity, in terms of molar ratio to the starting carboxylic acid halide, of the order of 1 to about 100, preferably of from 1.2 to 50.

After the reaction is completed, the reaction liquid is concentrated if desired and then a solvent which has little solvency to the product such as n-hexane is added thereto. The separated crystals are then separated. When crystals do not precipitate, water is added to the reaction liquid, and extraction with solvents such as dichloromethane and chloroform is carried out. Finally, the resulting crystals are purified according to any of the conventional methods such as recrystallization and chromatography to isolate the carboxylic acid esters represented by the general formula [I].

(2) Direct esterification process

A compound represented by the formula [II] or a salt thereof is reacted with an alcohol [IV] in the presence of an acid catalyst such as hydrochloric acid or sulfuric acid to prepare the compound [I].

Alternatively, a compound [II] and an alcohol [IV] are subjected to dehydration-condensation reaction in the presence of a condensation agent such as dicyclohexyl carbodiimide, diethylphosphoryl cyanide or diphenylphosphoryl azide to prepare the compound [I].

(3) Acid anhydride process

A compound [II] is reacted with ethyl chlorocarbonate and the like to form the corresponding mixed acid anhydride, which is further reacted with an alcohol (IV) to produce the compound [I].

(4) Active ester process

A compound [II] is reacted with 2,4-dinitrophenol, N-hydroxysuccinimide or the like to form the corresponding active ester, which is further reacted with an alcohol (IV) to produce the compound [I].

(5) Haloalkane process

The metal (e.g., sodium, potassium) salt or amine (e.g., triethylamine) salt of the compound [II] is reacted with a haloalkane (RX) to produce the compound [I].

(6) Cyclization process, disclosed in Japanese Unexamined Patent Publication No. 17,498/1977.

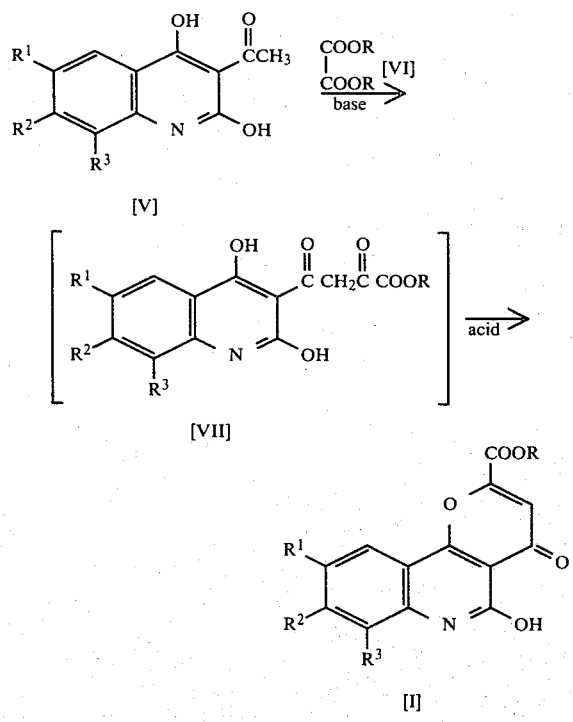

The compounds [I] are produced via the reaction formulas illustrated above. The substituents $R^1$, $R^2$, $R^3$, and R have been defined hereinbefore.

5. Antiallergic remedies for asthma

The compounds of the present invention are useful as antiallergic remedies for asthma or antasthmatics, as antiallergic agents, and as antiulcer agents.

The $LD_{50}$ of any of the present compounds is not less than 5000 mg/kg (rat, oral administration), and no abnormal symptone was observed on the prolonged toxicological test on rats at a dose of 800 mg/kg for one month. The compounds are thus expected to be safe pharmaceutical drugs.

With respect to the mode of administration, a dose each of 1 to 100 mg. is given orally 1 to 3 times a day; a dose each of 1 to 100 mg. is given rectally 1 to 3 times a day; a dose each of 1 to 50 mg. is given to the bronchus by inhalation 2 to 3 times a day; a dose each of 1 to 20 mg. is given intravenously 3 to 4 times a day; a dose each of 1 to 50 mg. is given to the nasal cavity 2 to 3 times a day; a dose each of 1 to 10 mg. is given as an eye-lotion 3 to 4 times a day; and a dose each of 1 to 50 mg. is applied as an ointment 2 to 3 times a day.

The dosage form of the present compounds is not restricted, and the compounds [I] are generally administered in the form of a composition containing conventional pharmaceutical products with acceptable additives such as carriers which include vehicles and other additives.

As described above, the compositions of the present invention are especially advantageous in that the compounds can be administered orally.

6. Examples

Preparation of 3-methyl-1-butyl ester of 7,8-dimethyl-5-hydroxy-quinolo[4,3-b]pyran-4-one-2-carboxylic acid (1) Preparation of 7,8-dimethyl-5-hydroxy-quinolo[4,3-b]pyran-4-one-2-carboxylic acid chloride (Step A)

One hundred (100) ml of thionyl chloride was added to 14.3 g of 7,8-dimethyl-5-hydroxy-quinolo[4,3-b]pyran-4-one-2-carboxylic acid, and the mixture was subjected to refluxing with stirring for 7 hours. The thionyl chloride was distilled away, and the resulting residue was dried. Then 50 ml of benzene was added to form a slurry, which was filtered. The resulting crystals were further washed 3 times with benzene and then dried to obtain pale-yellow crystals.

| Yield | 15.2 g (quantitative) |
|---|---|
| Melting point (m.p.) | 225°–232° C. (decomposed) |
| Infrared absorption (IR) | 3200–3100 cm$^{-1}$ |
| | 1780 cm$^{-1}$ |
| | 1680cm$^{-1}$, 1650cm$^{-1}$, 1620cm$^{-1}$ |

(2) Preparation of 3-methyl-1-butyl ester of 7,8-dimethyl-5-hydroxy-quinolo[4,3-b]pyran-4-one-2-carboxylic acid (Step B)

To 15.2 g of 7,8-dimethyl-5-hydroxy-quinolo[4,3-b]pyran-4-one-2-carboxylic acid chloride was added 175 ml of 3-methyl-1-butyl alcohol. The mixture was stirred for 40 minutes at a reaction temperature of 90° to 100° C. After cooling, 150 ml of n-hexane was added thereto. The resulting mixture was allowed to stand, and separated crystals were filtered. The crystals were recrystallized from chloroform-n-hexane to obtain 15.9 g of colorless crystals.

| | |
|---|---|
| Yield | 90% |
| m.p. | 236°–241° C. |
| I R | 2960cm$^{-1}$ |
| | 1695cm$^{-1}$, 1610cm$^{-1}$ |
| | 1245cm$^{-1}$ |
| Mass spe-ctrum(MS) | m/e (%) 355(61)M$^+$, 285(100) |

Other compounds of the present invention shown in the following tables were prepared substantially in the same manner as described above.

| Parent Carboxylic Acid | R | m.p. (°C.) | I R (cm$^{-1}$) | MS m/e(%) |
|---|---|---|---|---|
| 7,8-dimethyl-5-hydroxy-quinolo[4,3-b]pyran-4-one-2-carboxylic acid | 2-methyl-1-butyl | 253–255 | 2970 1695, 1610 1240 | 355(46)M$^+$ 285(100) |
| | 2,2-dimethyl-1-propyl | 272–279 | 2980 1695, 1615 1250 | 355(45)M$^+$ 285(100) |
| | 2-pentyl | 260–264 | 3200–2900 1700, 1615 1245 | 355(29)M$^+$ 285(100) |
| | 3-pentyl | 270–274 | 2980 1700, 1615 1250 | 355(23)M$^+$ 285(100) |
| | n-hexyl | 192–197 | 2960 1700, 1620 1250 | 369(60)M$^+$ 285(100) |
| | 4-methyl-1-pentyl | 217–220 | 2980 1700, 1620 1255 | 369(70)M$^+$ 285(100) |
| | 2-methyl-1-pentyl | 213–219 | 2975 1700, 1615 1245 | 369(47)M$^+$ 285(100) |
| | 3-methyl-1-pentyl | 199–204 | 2960 1690, 1610 1250 | 369(81)M$^+$ 285(100) |
| | 4-methyl-2-penty | 242–249 | 2970 1700, 1615 1255 | 369(15)M$^+$ 285(100) |
| | 2-hexyl | 203–209 | 2970–2940 1700, 1615 1250 | 369(19)M$^+$ 285(100) |
| | 3-hexyl | 250–256 | 2970 1700, 1615 1250 | 369(24)M$^+$ 385(100) |
| | 3-methyl-2-pentyl | 259–265 | 2970 1700, 1610 1250 | 369(35)M$^+$ 285(100) |
| 9-methyl-5-hydroxy-quinolo[4,3-b]pyran-4-one-2-carboxylic acid | 3-methyl-1-butyl | 228–231 | 2980–2900 1700, 1440 1260 | 341(100)M$^+$ 271(93) 243(47) |
| | 2-methyl-1-butyl | 212–217 | 2980–2800 1700, 1430 1260 | 341(88)M$^+$ 271(100) 243(48) |
| | 2,2-dimethyl-1-propyl | 277–282.5 | 3000–2820 1700, 1430 1255 | 341(73)M$^+$ 271(100) 243(33) |
| | 2-pentyl | 212–216 | 3000–2820 1700, 1430 1260 | 341(35)M$^+$ 271(100) 243(44) |
| | 2-methyl-1-pentyl | 197–201 | 3000–2840 1700, 1435 1255 | 355(59)M$^+$ 241(100) 243(33) |
| | 3-hexyl | 182–188 | 3000–2820 1705, 1430 1255 | 355(20)M$^+$ 271(100) 243(26) |
| 9-chloro-5-hydroxy-quinolo[4,3-b]pyran-4-one-2-carboxylic acid | 3-methyl-1-butyl | 292–300 | 3220, 2980 1720, 1435 1260 | 362(39) ⎫ M$^+$ 361(100) ⎭ 292(35) 291(92) |
| 9-ethoxycarbonyl-5-hydroxy-quinolo[4,3-b]pyran-4-one-2-carboxylic acid | 3-methyl-1-butyl | 234–237 | 3220, 2980 1710, 1615 1250 | 399(100)M$^+$ 354(34) 329(19) 301(21) 284(64) |
| 9-n-butyl-5-hydroxy-quinolo[4,3-b]pyran-4-one-2-carboxylic acid | 3-methyl-1-butyl | 218–220 | 2980–2840 1705, 1435 1255 | 383(90)M$^+$ 340(100) 270(98) |
| 8,9-dimethoxy-5-hydroxy-quinolo[4,3-b]pyran-4-one-2-carboxylic acid | 3-methyl-1-butyl | 272–276 | 3210, 2980 1710, 1690 1280, 1260 | 387(100)M$^+$ 372(14) 317(39) 302(44) |
| 9-methoxy-5-hydroxy- | | 237–239 | 3000–2840 | 357(100)M$^+$ |

-continued

| Parent Carboxylic Acid | R | m.p. (°C.) | I R (cm$^{-1}$) | MS m/e(%) |
|---|---|---|---|---|
| quinolo[4,3-b]pyran-4-one-2-carboxylic acid | 3-methyl-1-butyl | | 1700<br>1300–1230 | 287(92)<br>272(63) |

What is claimed is:

1. An ester derivative of quinolopyran-4-one-2-carboxylic acids which is represented by the formula [I] or a tautomer thereof

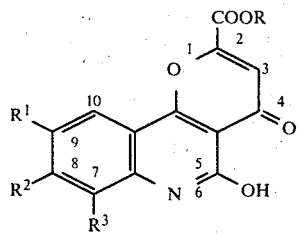

wherein, $R^1$, $R^2$ and $R^3$ each stand for hydrogen, an alkyl group having 1 to 5 carbon atoms, an alkoxyl group having 1 to 5 carbon atoms, benzyloxy group, a halogen atom, an alkoxycarbonyl group having 2 to 6 total carbon atoms, an aryl group having 6 to 10 carbon atoms, or an alkylenedioxy group having 1 to 3 carbon atoms formed by two alkoxyl groups which are selected from $R^1$, $R^2$ and $R^3$ and bonded together, respectively; and R is an alcohol residue having 5 or 6 carbon atoms selected from the group consisting of 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl, and 3-methyl-2-pentyl.

2. The ester derivative as set forth in claim 1, which is selected from the group consisting of 9-methyl-5-hydroxy-quinolo[4,3-b]pyran-4-one-2-carboxylic acid [R] ester,
8-methyl-5-hydroxy-quinolo[4,3-b]pyran-4-one-2-carboxylic acid [R] ester,
7-methyl-5-hydroxy-quinolo[4,3-b]pyran-4-one-2-carboxylic acid [R] ester,
9-ethyl-5-hydroxy-quinolo[4,3-b]pyran-4-one-2-carboxylic acid [R] ester,
9-n-butyl-5-hydroxy-quinolo[4,3-b]pyran-4-one-2-carboxylic acid [R] ester,
9-t-butyl-5-hydroxy-quinolo[4,3-b]pyran-4-one-2-carboxylic acid [R] ester,
7,8-dimethyl-5-hydroxy-quinolo[4,3-b]pyran-4-one-2-carboxylic acid [R] ester,
7,9-dimethyl-5-hydroxy-quinolo[4,3-b]pyran-4-one-2-carboxylic acid [R] ester,
9-methoxy-5-hydroxy-quinolo[4,3-b]pyran-4-one-2-carboxylic acid [R] ester,
7-methoxy-5-hydroxy-quinolo[4,3-b]pyran-4-one-2-carboxylic acid [R] ester,
8,9-dimethoxy-5-hydroxy-quinolo[4,3-b]pyran-4-one-2-carboxylic acid [R] ester,
9-butoxy-5-hydroxy-quinolo[4,3-b]pyran-4-one-2-carboxylic acid [R] ester,
8,9-methylenedioxy-5-hydroxy-quinolo[4,3-b]pyran-4-one-2-carboxylic acid [R] ester,
9-benzyloxy-5-hydroxy-quinolo[4,3-b]pyran-4-one-2-carboxylic acid [R] ester,
9-chloro-5-hydroxy-quinolo[4,3-b]pyran-4-one-2-carboxylic acid [R] ester,
7-chloro-5-hydroxy-quinolo[4,3-b]pyran-4-one-2-carboxylic acid [R] ester,
9-bromo-5-hydroxy-quinolo[4,3-b]pyran-4-one-2-carboxylic acid [R] ester,
9-fluoro-5-hydroxy-quinolo[4,3-b]pyran-4-one-2-carboxylic acid [R] ester,
9-ethoxycarbonyl-5-hydroxy-quinolo[4,3-b]pyran-4-one-2-carboxylic acid [R] ester,
7-methyl-8-chloro-5-hydroxy-quinolo[4,3-b]pyran-4-one-2-carboxylic acid [R] ester, and
9-phenyl-5-hydroxy-quinolo[4,3-b]pyran-4-one-2-carboxylic acid [R] ester;
wherein the symbol [R] stands for 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl, or 3-methyl-2-pentyl.

3. The tautomer of the ester derivative as set forth in claim 1, which is represented by the general formula,

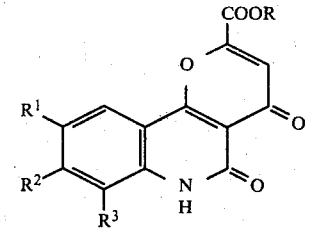

wherein, $R^1$, $R^2$ and $R^3$ as well as R are as defined in claim 1.

4. The ester derivative as set forth in claim 1, 2 or 3, in which the substituent R is selected from the group consisting of 3-methyl-1-butyl, 2-methyl-1-butyl, 2,2-dimethyl-1-propyl, 2-pentyl, 2-methyl-1-pentyl, 2-hexyl and 3-hexyl.

5. An antiallergic composition for asthma which comprises an effective amount for the treatment of allergic asthma of an ester derivative of quinolopyran-4-one-2-carboxylic acids represented by the general formula [I] or a tautomer of the ester derivative,

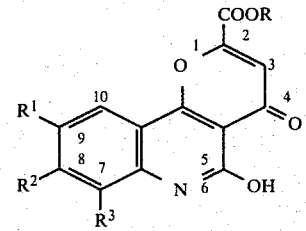

wherein $R^1$, $R^2$ and $R^3$ each stand for hydrogen, an alkyl group having 1 to 5 cargon atoms, an alkoxy group having 1 to 5 carbon atoms, benzyloxy group, a halogen atom, an alkoxycarbonyl group having 2 to 6 total carbon atoms, an aryl group having 6 to 10 carbon atoms, or an alkylenedioxy group having 1 to 3 carbon atoms formed by two alkoxyl groups which are selected from $R^1$, $R^2$ and $R^3$ and bonded together, respectively;

and R is an alcohol residue having 5 or 6 carbon atoms selected from the group consisting of 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl and 3-methyl-2-pentyl; and a pharmaceutically acceptable carrier.

6. The antiallergic composition as set forth in claim 5, in which the ester derivative is selected from the group consisting of 9-methyl-5-hydroxy-quinolo[4,3-b]pyran-4-one-2-carboxylic acid [R] ester,
8-methyl-5-hydroxy-quinolo[4,3-b]pyran-4-one-2-carboxylic acid [R] ester,
7-methyl-5-hydroxy-quinolo[4,3-b]pyran-4-one-2-carboxylic acid [R] ester,
9-ethyl-5-hydroxy-quinolo[4,3-b]pyran-4-one-2-carboxylic acid [R] ester,
9-n-butyl-5-hydroxy-quinolo[4,3-b]pyran-4-one-2-carboxylic acid [R] ester,
9-t-butyl-5-hydroxy-quinolo[4,3-b]pyran-4-one-2-carboxylic acid [R] ester,
7,8-dimethyl-5-hydroxy-quinolo[4,3-b]pyran-4-one-2-carboxylic acid [R] ester,
7,9-dimethyl-5-hydroxy-quinolo[4,3-b]pyran-4-one-2-carboxylic acid [R] ester,
9-methoxy-5-hydroxy-quinolo[4,3-b]pyran-4-one-2-carboxylic acid [R] ester,
7-methoxy-5-hydroxy-quinolo[4,3-b]pyran-4-one-2-carboxylic acid [R] ester,
8,9-dimethoxy-5-hydroxy-quinolo[4,3-b]pyran-4-one-2-carboxylic acid [R] ester,
9-butoxy-5-hydroxy-quinolo[4,3-b]pyran-4-one-2-carboxylic acid [R] ester,
8,9-methylenedioxy-5-hydroxy-quinolo[4,3-b]pyran-4-one-2-carboxylic acid [R] ester,
9-benzyloxy-5-hydroxy-quinolo[4,3-b]pyran-4-one-2-carboxylic acid [R] ester,
9-chloro-5-hydroxy-quinolo[4,3-b]pyran-4-one-2-carboxylic acid [R] ester,
7-chloro-5-hydroxy-quinolo[4,3-b]pyran-4-one-2-carboxylic acid [R] ester,
9-bromo-5-hydroxy-quinolo[4,3-b]pyran-4-one-2-carboxylic acid [R] ester,
9-fluoro-5-hydroxy-quinolo[4,3-b]pyran-4-one-2-carboxylic acid [R] ester,
9-ethoxycarbonyl-5-hydroxy-quinolo[4,3-b]pyran-4-one-2-carboxylic acid [R] ester,
7-methyl-8-chloro-5-hydroxy-quinolo[4,3-b]pyran-4-one-2-carboxylic acid [R] ester, and
9-phenyl-5-hydroxy-quinolo[4,3-b]pyran-4-one-2-carboxylic acid [R] ester;

wherein the symbol [R] stands for 3-methyl-1-butyl, 2-methyl-1-butyl, 2,2-dimethyl-1-propyl, 2-pentyl, 3-pentyl, n-hexyl, 4-methyl-1-pentyl, 2-methyl-1-pentyl, 3-methyl-1-pentyl, 4-methyl-2-pentyl, 2-hexyl, 3-hexyl, or 3-methyl-2-pentyl.

7. The antiallergic composition as set forth in claim 5, in which the tautomer of the ester derivative is represented by the general formula,

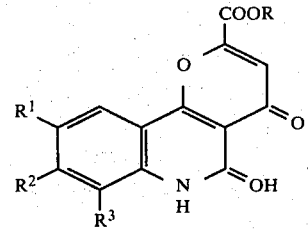

wherein, $R^1$, $R^2$ and $R^3$ as well as R are as defined in claim 5.

8. The antiallergic composition as set forth in claim 5, 6 or 7, in which the substituent R is selected from the group consisting of 3-methyl-1-butyl, 2-methyl-1-butyl, 2,2-dimethyl-1-propyl, 2-pentyl, 2-methyl-1-pentyl, 2-hexyl and 3-hexyl.

9. The antiallergic composition as set forth in claim 5, which is to be administered orally.

* * * * *

UNITED STATES PATENT AND TRADEMARK OFFICE
CERTIFICATE OF CORRECTION

PATENT NO. : 4,298,610
DATED : November 3, 1981
INVENTOR(S) : YASUHIRO MORINAKA ET AL It is certified that error appears in the above—identified patent and that said Letters Patent is hereby corrected as shown below:

Column 16, lines 25 to 30, in the lower right hand corner of the structural formula, please correct the formula as follows:

Delete " 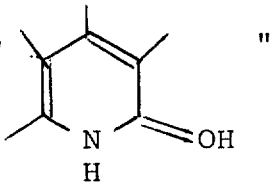 "      and insert -- 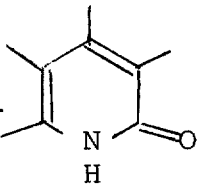 --.

[SEAL]

Signed and Sealed this

Twenty-fifth Day of May 1982

Attest:

Attesting Officer

GERALD J. MOSSINGHOFF
Commissioner of Patents and Trademarks